United States Patent [19]

Bockowski et al.

[11] Patent Number: 4,851,583
[45] Date of Patent: Jul. 25, 1989

[54] METHOD OF GENERATING ACROLEIN

[75] Inventors: Edmund Bockowski, Furlong, Pa.; Cato R. McDaniel, The Woodlands, Tex.

[73] Assignee: Betz Laboratories, Inc., Trevose, Pa.

[21] Appl. No.: 140,450

[22] Filed: Jan. 4, 1988

[51] Int. Cl.$^4$ .................. C07C 45/51; C07C 45/56
[52] U.S. Cl. ............................. 568/465; 568/468; 568/485; 43/124
[58] Field of Search ............... 568/450, 465, 485, 468; 43/124

[56] References Cited

U.S. PATENT DOCUMENTS

| | | | |
|---|---|---|---|
| 2,959,476 | 11/1960 | Van Overbeck | 71/2.7 |
| 3,189,655 | 6/1965 | Thompson | 568/468 |
| 3,250,667 | 5/1966 | Legator | 162/190 |
| 3,298,906 | 1/1967 | Knowles | 167/22 |
| 3,380,462 | 4/1968 | Schieber et al. | 137/3 |
| 3,690,857 | 9/1972 | Blair | 71/66 |
| 4,071,563 | 1/1978 | Kummer et al. | 568/450 |
| 4,307,252 | 12/1981 | Weber et al. | 568/450 |

FOREIGN PATENT DOCUMENTS 1049421 11/1966 United Kingdom ............... 568/485

OTHER PUBLICATIONS

Howell, G. R. and Weston-Webb, P. L., "Chesapeake Corp. Finds Acrolein Biocide an Effective, Economical Chlorine Substitute"*Paper Trade Journal*, 160 : 40–43 (1976).

Walko, J. F. & Smith, W. L., "Double-Duty Slimicide", *Power Engineering*, 63:40–41 (1969).

Huet et al., "Wet Silica Gel, A Convenient Reagent for Deacetalization", *Synthesis* 1978 (1) 63–65.

Herberle, R. A., "Acrolein : An Effective Cooling Water Slimicide", *The Betz Indicator* vol. 36 No. 9 (1969).

Naflon Product Bulletin, DuPont Company May 1983. "Naflon Membranes" Aldrichimica Acta 18:1 p. 24 (1985).

*Primary Examiner*—Werren B. Lone
*Attorney, Agent, or Firm*—Alexander D. Ricci; Roslyn T. Tobe

[57] ABSTRACT

This invention relates to the generation of acrolein from an acetal of acrolein via exposure to a sulfonic acid reusable catalytic material. The acrolein acetals have the following general structures;

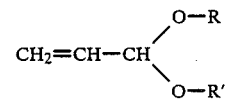

where R may or may not be equal to R' R/R' is an alkyl group having from 1 to 6 carbons; and

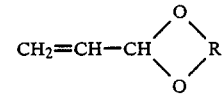

where R is a cyclic diol derived from ethylene glycol, propylene glycol, butylene glycol, pentylene glycol, hexylene glycol, glycerol hexoses or polyaccharides.

9 Claims, No Drawings

METHOD OF GENERATING ACROLEIN

Acrolein is a well-known pesticide used to treat liquids containing slime-forming microorganisms. As used herein, the term "pesticide" means: (1) any substance or mixture of substances intended for preventing, destroying, repelling or mitigating any pest, and (2) any substance or mixture of substances intended for use as a plant regulator, defoliant or desiccant. As used herein, the term "pest" means: (1) any insect, rodent, nematode, fungus, weed, or (2) any other form of terresterial or aquatic plant or animal life or virus, bacteria or other microorganism. Although a highly effective pesticide, the use of acrolein has been severely impeded by its hazardous properties. In the first instance, acrolein vapors are highly volatile, poisonous when inhaled, and extremely irritating to the eyes, skin and respiratory tract. In addition, these vapors form a highly combustible admixture in air over a broad percentage range and, consequently, represent a pronounced fire, and explosion hazard. The physiological potency of acrolein is demonstrated by the fact that exposure to a vapor concentration of 0.25 ppm for a period of 5 minutes causes moderate irritation, a concentration of 1 ppm causes painful irritation in the same period of time, and a concentration of 150 ppm for 10 minutes is believed to be fatal to humans. The fire-explosion hazard which it presents is demonstrated by a flash point of less than 0° F.

These conditions, when combined with the availability of acrolein in tank cars, conventional steel drums, and like containers, have seriously retarded the commercial utilization of acrolein as a biocidal agent. Usually, the limited quantities involved and the requirement to employ expensive safety systems and to train personnel in the safe handling of this material are also deterrents to the widespread use of this pesticide in many applications. A number of proposed methods of use have been plagued by the very real possibility of the rupture or leaking of the storage and feeding equipment employed, with consequent probability of toxicity to personnel or animals and/or fire-explosion damage to plants and equipment. Even if the fatal consequences of inhalation, fire or explosion are avoided, the irritation and lachrymation caused by even minute quantities of escaped vapors are a pronounced disadvantage. Similarly, equipment such as air purifying respirators or supplied air breathing equipment would be required during the startup of the treatment, and explosion-proof equipment would be necessitated in all areas adjacent to the apparatus for the storage and feed of acrolein. Furthermore, air accelerates the polymerization of this product, thereby reducing its availability. Elaborate equipment is required for the purpose of avoiding the formation of an air-vapor admixture within the storage and feeding systems.

A special system such as that described in U.S. Pat. No. 3,380,462, Schieber et al., was designed to utilize acrolein in a safe manner. Even this elaborate system to isolate acrolein and prevent its escape was plagued by accidental releases resulting in employee exposure and minor health effects.

Acrolein itself is an excellent pesticide and fairly economical. The advent of increased environmental concern and regulation further diminished the use of acrolein as a pesticide. Acrolein was designated a harzardous substance by the Environmental Protection Agency (EPA) pursuant to the Federal Water Pollution Control Act. Discharge of as little as one pound of acrolein may be subject to both criminal and civil penalties. For example, a civil penalty for discharging one poiund of acrolein in any 24-hour period may be as much as $5,000 or the Administrator of the EPA may impose a criminal penalty of up to $50,000 for each 24 hours period involved.

These fines and the risks associated with acrolein prompted Betz Laboratories, Inc., the assignee of this application, to discontinue its highly successful acrolein treatment programs. As described in an article by G. R. Howell and P. L. Weston-Webb, Jr., "Chesapeake Corp. Finds Acrolein Biocide an Effective Economical Chlorine Substitute", *Paper Trade Journal,* 160:40–43 (1976), and an article by J. F. Walko and W. L. Smith, "Double-Duty Slimicide", *Power Engineering,* 63:40–41 (1969); these treatment programs were successfully used in a paper mill to replace chlorine as a biological control as well as in cooling water as a slimicide.

Acrolein has advantages over chlorine, a common pesticide utilized in many aqueous systems. Unlike chlorine, acrolein is less reactive with oxidizable materials or other chemical constituents usually found in both surface and well water supplies. Chlorination alone is often uneconomical for pest control in systems using waters with high chlorine demands, or in systems heavily contaminated by process leakage. In addition, chlorine is frequently not very effective against filamentous algae, bacteria and shellfish in heavily contaminated systems.

Acrolein has a broad spectrum of biological activity. The breadth of acrolein's effectiveness is amply disclosed by U.S. Pat. Nos. 2,959,476, Van Overbeck, and 3,250,667, Legator. Acrolein has been found to effectively control bacteria such as *Bacillus subtilis, Pseudomonas putrefaciens* and *Escherichia col.;* fungi such as *Penicillium italicum, Sacchromyces cereviseae* and *Helminthosporium turcicum;* algae; macroinvertebrates such as snails and clams; and aquatic plants and weeds. Acrolein is also more effective than chlorine in controlling macroinvertebrates and submerged, as well as floating, aquatic weeds and algae. Other uses may be envisioned for acrolein produced from a low harzard precursor such as its use as a grain or soil fumigant for control of fungi in wood which is in contact with the ground or as a room temperature sterilizing agent for medical equipment or supplies.

From an environmental point of view, acrolein is a good pesticide because it is effective, detoxified readily and cheaply, and is environmentally non-persistent. Water solutions of acrolein are readily and conveniently neutralized for disposal with sodium bisulfite. This reaction produces a nontoxic water-soluble salt. For these reasons, there has been renewed interest in creating a process to generate acrolein froma precursor that is safe to handle.

One method of generating acrolein from a safe to handle precursor is to deacetalize an acrolein acetal. It is known in the art that aldehydes, such as acrolein, may be recovered by deacetalization of the corresponding acetal. Deacetalization procedures are known in the art and have been described as generally involving hydrolysis in an acidic medium or transacetalization. The mechanism of deacetalization is believed to proceed by protonation of one of the alkoxy groups of the acetal. Thus, the stronger the acid the more effective the deacetalization will be.

It is also known that not all aldehydes are easily recovered, or recovered in good yield following deacetalization. For example, the recovery of acrolein from the hydrolysis of acrolein acetals such as dimethyl or diethyl acetals in dilute aqueous acid is fraught with difficulty and results in poor yields of acrolein. This may be caused in part by prolonged contact of the acrolein with the acids used in the deacetalization. Acrolein is a very reactive chemical with a pronounced tendency to form polymers and by-products such as hydracrylaldehyde and 3-formyl-4-tetrahydropyranol from a mildly acidic aqueous acrolein solution.

Huet et al., disclose a method for obtaining an aldehyde from the corresponding acetal utilizing hydrolysis on wet silica gel or alumina columns. Huet et al., "Wet Silica Gel, A Convenient Reagent for Deacetalization", Synthesis 1978 (1), 63–65. It is noted that Huet et al., utilizes oxalic and sulfuric acid in addition to wet silica gel to speed the deacetalization reaction and improve yields. Huet et al., do not teach this method for generating acrolein from its acetal. The use of the previously described methods of deacetalization to generate acrolein from its acetal will not provide a practical source of acrolein.

The use of acrolein acetals has been described in U.S. Pat. Nos. 3,298,906 to Knowles and 3,690,857 to Blair. The U.S. Pat. No. 3,298,906 describes using an acrolein diethyl acetal to control nematodes in soil. The U.S. Pat. No. 3,698,857 describes a method of treating aquatic life and plant with an acrolein acetal as a method to avoid killing fish present in the system. Neither of these patents suggest the conversion of the acrolein acetal to acrolein for biocidal purposes.

SUMMARY OF THE INVENTION

The present invention seeks to overcome the problem of low yields and provide a simple, economical method of generating acrolein.

The present invention relates to the generation of acrolein from an acetal of acrolein via exposure to suitable non-silica acidic catalytic surfaces. On exposure to the suitable non-silica acidic catalytic surface, the acetal of acrolein will hydrolyze and release acrolein. The key step in the production of acrolein is the use of suitable non-silica acidic catalytic surfaces to generate the release of the desired acrolein from its acetal rapidly at near neutral pH and ambient temperature. Acrolein acetals have a lower vapor pressure, higher flash point, lower toxicity, and are not lachrymatory. Consequently, they are safe to handle as opposed to the highly volatile and hazardous acrolein. It is an object of the invention to provide a method of generating usable acrolein from a precursor which is not harardous. A further object of the invention is to provide a means of pest control incorporating the method of generating acrolein from acetals of acrolein.

Another object of the invention is to provide a method of generating acrolein from an acetal of acrolein in high yield with minimal polymeration or by-products. One of the advantages over the prior act offered by the present invention is the near neutral pH conditions of the reaction unlike the method of Huet et. al which needs the addition of oxalic or sulfuric acid in order to effectively generate acrolein from its acetal.

DETAILED DESCRIPTION OF INVENTION

The present invention relates to the generation of acrolein from an acrolein acetal. Acrolein acetals which would be effective for utilization in the process have the general structure

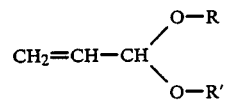

where R may or may not be equal to R' and R/R' is an alkyl group having from 1 to 6 carbons. Preferably, R equals R' and is an alkyl group having from 1 to 2 carbons. Cyclic acrolein acetals are also believed to be suitable for use in generating acrolein from this process. These acrolein acetals have the following general structure

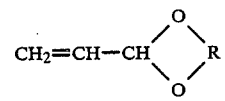

where the R group completes a cyclic structure derived from selected diols such as ethylene glycol, propylene glycol, butylene glycol, pentylene glycol, hexylene glycol, glycerol, hexoses or polysaccharides. Cyclic acetals though to be effective for use in the present invention are ethylene glycol acrolein acetal and propylene glycol acrolein acetal.

Acrolein acetals are safe to handle and do not present the toxicity and high vapor pressure problems that acrolein has. It is thought that acrolein acetals will rapidly hydrolyze in the presence of a suitable non-silica catalytic acidic surface to yield acrolein and alcohol. The release of acrolein in accordance with the present invention is generally described by the following reaction:

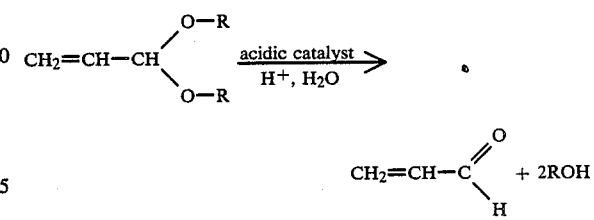

The key to the present invention is the use of an acidic reusable catalytic surface such as an ion exchange resin with sulfonic acid groups, at near neutral pH. The acid groups on the catalysts of this invention are superacidic, preferably sulfonic acid groups. Exemplary sources of such superacidic groups are resins, membranes, or liquids which contain sulfonic acid groups. The catalyst resins, membranes or liquids facilitate the production of the acrolein in high yeilds by preventing the undesirable prolonged contact of acrolein with acids, such as in the prior art deacetalization procedures.

Additionally, these catalysts already contain sulfonic acid thereby obviating the extra step of adding acid as is the case when silica gel is utilized. On example of such a material is a pefluorinated ion exchange resin-sulfonic acid catalyst, such as NAFION, a trademark of E. I. DuPont de Nemours & Co., Inc., available from Aldrich Chemical Company.

NAFION perfluorinated membranes are fabricated from copolymers of tetrafluorethylene and perfluorinated monomers containing sulfonic acid groups. The perfluorinated membranes are composed of carbonfluorine backbone chains with perfluoro side chains containing sulfonic groups. The chemical structure is shown below:

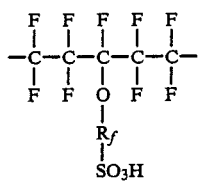

Attached to the fluoropolymer chains are perfluorinated cation exchange sites. The polymer is permeable to many cations and polar compounds, but remains impermeable to anions and nonpolar species. The perfluorinated membranes are strong polymeric acids which react with organic and inorganic bases, however; the sulfonic acid groups in the polymer are essentially immobile and immersed in a fluorocarbon matrix. The acrolein acetal would be exposed to the NAFION resin beads or membrane, and catalytically hydrolyzed with water. It is further postulated that ion exchange resins or liquid ion exchangers with sulfonic acid groups such as polyvinyl sulfonic acid copolymers of sulfonated styrene copolymers will function as a suitable acidic, non-silica catalytic surface, if the water solubility of the copolymers is minimized or retarded. Finally, it is postulated that highly water insoluble organics, similar in chemical structure to alkyl benzene sulfonic acids, could be produced for the practice of this invention.

The uses of acrolein have been well documented as a pesticide and as an herbicide. Acrolein generated by acidic hydrolysis of acrolein acetals may be utilized to treat an aqueous system or other systems which use acrolein as a treatment for pests. One method, which would provide dilute acrolein in situ to the target system, would be to contact the acetal either in dilute or neat form with deionized water to achieve a proper dilution, then contact the diluted acrolein acetal with the suitable acidic catalyst to produce acrolein which may then be utilized in the treatment of an aqueous system. Another possible use of acrolein generated by acidic hydrolysis would be as a fumigant.

The following examples are illustrative of the invention.

Example 1

A 1200 ug/mL solution of the diethylacetal of acrolein was prepared by the addition of 0.12 g of acrolein diethylacetal to a 100 mL volumetric flask which was then brought to volume with water. One mL of the 1200 ug/mL acrolein diethylacetal solution was treated with 0.2 g of NAFION NR-50 resin bead (10-35 mesh) obtained from Aldrich Chemical. This sample was analyzed by gas chromatography/mass spectrometry (GC/MS) using a Finnegan 4600 GC/MS system. Chromatography was performed using a 1 uL split injection onto a 30 metre×0.25 mm DB-1 fused silica open tubular capillary column. Mass spectra were obtained by scanning from 35 to 350 dalton (AMU) each second. The chromatogram of this sample exhibited a peak at 56 seconds which was identified as acrolein by comparison with a known sample of acrolein. The mass spectrum of this peak was consistent with that of acrolein. In addition, the peak assigned to the acrolein acetal has completely disappeared. It is believed that the conversion is essentially complete within five minutes under the conditions employed. The hydrolysis took place so rapidly that kinetics could not be established. The data obtained indicate no detectable amount of residual acrolein diethyl acetal.

Example 2

A 40 mL sample of a 1680 ug/mL solution of acrolein diethylacetal (3, 3-diethoxy-l-propene) was treated with 1 g of NAFION 410 for 15 minutes. The solution was then analyzed by gas chromatography to determine the quantity of acrolein produced. It was determined that 1680 ug/mL of acrolein diethylacetal produces 775 ug/mL of acrolein. The theoretical yield is 772 ug/mL thus the experiment produced slightly more than 100% yield which is within the experimental limits of +/−5−10%.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

What is claimed is:

1. A method for producing acrolein comprising contacting an acrolein acetal selected from the group consisting of

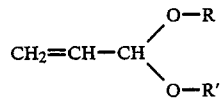

where R may be equal to R' and R/R' is an alkyl group having 1 to 6 carbons and

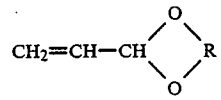

where R is a cyclic diol derived from ethylene glycol, propylene glycol, butylene glycol, pentylene glycol, hexylene glycol, glycerol, hexoses or polysaccharides; with a sulfonic acid catalytic material which will convert said acrolein acetal into acrolein at ambient temperature and atmospheric pressure.

2. A method as described in claim 1 wherein said acrolein acetal is selected from the group consisting of dimethyl acrolein acetal, diethyl acrolein acetal, ethylene glycol acrolein acetal and propylene glycol acetal.

3. A method as described in claim 2 wherein said sulfonic acid catalytic material comprises an ion-exchange resin.

4. A method as described in claim 3 wherein said ion-exchange resin comprises a perfluorosulfonic acid cation ion exchange resin.

5. A method for producing acrolein comprising contacting an aqueous solution of an acrolein acetal selected from the group consisting of dimethyl acrolein acetal, diethyl acrolein acetal, ethylene glycol acetal and propylene glycol acetal with a sulfonic acid catalytic material at ambient temperature and atmospheric pressure, wherein said sulfonic acid catalytic material is in the form of a resin, membrane or liquid which will hydrolyze said acrolein acetal into acrolein.

6. A method as described in claim 5 wherein said sulfonic acid catalytic material comprises a perfluorosulfonic acid cation ion exchange resin.

7. A method for producing acrolein comprising contacting an aqueous solution of an acrolein acetal with a sulfonic acid catalytic materials which will convert said acrolein acetal into acrolein at ambient temperature and atmospheric pressure.

8. A method as described in claim 7 wherein said acrolein acetal is selected from the group consisting of dimethyl acrolein acetal, diethyl acrolein acetal, ethylene glycol acrolein acetal and propylene glycol acrolein acetal.

9. A method as described in claim 8 wherein said sulfonic acid catalytic material comprises a perfluorosulfonic acid cation ion exchange resin.

* * * * *